(12) United States Patent
Komata et al.

(10) Patent No.: US 7,385,091 B2
(45) Date of Patent: Jun. 10, 2008

(54) PROCESS FOR PRODUCING FLUORINE-CONTAINING DIOL AND ITS DERIVATIVES

(75) Inventors: Takeo Komata, Kawagoe (JP); Makoto Matsuura, Kawagoe (JP); Kei Matsunaga, Kawagoe (JP)

(73) Assignee: Central Glass Co., Ltd., Ube-shi (JP)

( * ) Notice: Subject to any disclaimer, the term of this patent is extended or adjusted under 35 U.S.C. 154(b) by 109 days.

(21) Appl. No.: 11/497,375

(22) Filed: Aug. 2, 2006

(65) Prior Publication Data

US 2007/0032684 A1 Feb. 8, 2007

(30) Foreign Application Priority Data

Aug. 3, 2005 (JP) ............................. 2005-225032

(51) Int. Cl.
*C07C 35/18* (2006.01)
(52) U.S. Cl. .................................................. 568/826
(58) Field of Classification Search ................. 568/812
See application file for complete search history.

(56) References Cited

U.S. PATENT DOCUMENTS

| 3,662,071 | A | 5/1972 | Langkammerer |
| 6,784,312 | B2 | 8/2004 | Miyazawa et al. |
| 2005/0215836 | A1* | 9/2005 | Komata et al. ............. 568/812 |

FOREIGN PATENT DOCUMENTS

JP          2003-40840 A     2/2003

\* cited by examiner

*Primary Examiner*—Yvonne Eyler
*Assistant Examiner*—Kellette Gale
(74) *Attorney, Agent, or Firm*—Crowell & Moring LLP

(57) ABSTRACT

A process for producing a fluorine-containing diol represented by the formula [2],

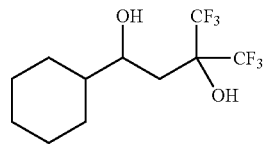

includes reducing a hydroxy ketone represented by the formula [1],

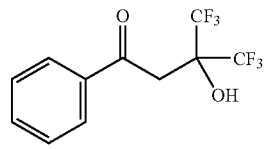

by hydrogen in the presence of a ruthenium catalyst. The ruthenium catalyst may be a solid-phase catalyst in which ruthenium is carried on an activated carbon, alumina or silica.

20 Claims, No Drawings

PROCESS FOR PRODUCING FLUORINE-CONTAINING DIOL AND ITS DERIVATIVES

BACKGROUND OF THE INVENTION

The present invention relates to a process for producing a fluorine-containing diol, which is a compound useful as a raw material for monomers adapted to the next generation photoresists.

It is known that esters, which are formed by the bonding of fluorine-containing diols and acrylic acid derivatives (including acrylic acid and methacrylic acid), have bright prospects as monomer raw materials of the next generation resist materials and that resists containing such esters as their constituent element are superior in light transmission and surface adhesion (see U.S. Pat. No. 6,784,312 corresponding to Japanese Patent Laid-open Publication 2003-040840).

U.S. Pat. No. 3,662,071 discloses a process for synthesizing α-[(2-hydroxy-1-methyl-3,3,3-trifluoro-2-trifluoromethyl)propyl]benzyl alcohol by the steps of (a) heating hexafluoroacetone and propiophenone at 160° C.; and (b) reducing the product of the step (a) by aluminum isopropoxide using isopropanol as a solvent.

U.S. Patent Application Publication No. U.S. 2005/0215836 A1 discloses a process for producing a fluorine-containing 2,4-diol by reducing a hydroxy ketone by hydrogen in the presence of a ruthenium catalyst.

SUMMARY OF THE INVENTION

It is an object of the present invention to provide a process for producing a fluorine-containing diol, which is suitable for an industrial scale production thereof.

According to the present invention, there is provided a first process for producing a fluorine-containing diol represented by the formula [2], that is, 1-cyclohexyl-4,4,4-trifluoro-3-(trifluoromethyl)butane-1,3-diol.

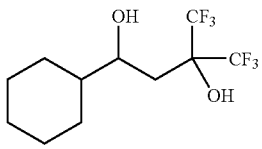

[2]

The first process comprises reducing a hydroxy ketone represented by the formula [1],

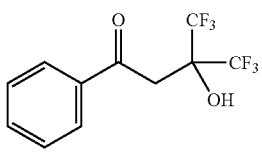

[1]

by hydrogen in the presence of a ruthenium catalyst.

DETAILED DESCRIPTION

In the step (b) of the process of U.S. Pat. No. 3,662,071, the product of the step (a) of this patent is reduced by a large amount of aluminum isopropoxide using isopropanol as a solvent. This causes a problem of the generation of wastes (e.g., aluminum wastes and an organic waste water) in large amounts. Thus, the process of U.S. Pat. No. 3,662,071 is cumbersome to be conducted in an industrial scale production.

In view of the above-mentioned problem of the prior art technique, the present inventors have eagerly studied the process for producing a fluorine-containing diol represented by the formula [2], which is suitable for an industrial scale production thereof As a result, we have unexpectedly found that the target compound can be produced by an easy operation of the above first process under a mild reaction condition with high yield and with less amounts of wastes.

If the target fluorine-containing diol of the present invention, which is represented by the formula [2], is produced by the process of U.S. 2005/0215836 A1, a skilled person will use a starting compound represented by the formula [7].

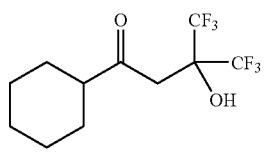

[7]

This starting material corresponds to the hydroxy ketone of U.S. 2005/0215836 A1, which is represented by the following formula,

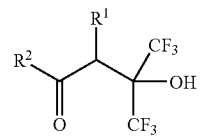

wherein $R^1$ is H, and $R^2$ is a cyclohexyl group. This starting material is, however, very expensive in price, and its obtainment in large amount is difficult.

In view of the above-mentioned problem of the prior art technique, the present inventors have eagerly continued research. With this, we unexpectedly found that the fluorine-containing diol represented by the formula [2] can be produced by bringing the hydroxy ketone represented by the formula [1] into contact with hydrogen in the presence of a ruthenium catalyst. In fact, it was found in this reaction that the phenyl group of the hydroxy ketone is unexpectedly hydrogenated or reduced into the cyclohexyl group of the fluorine-containing diol.

The hydroxy ketone represented by the formula [1] is a compound that can be produced with a very low price from raw materials of hexafluoroacetone and acetophenone. Therefore, the target fluorine-containing diol represented by the formula [2] can be produced by the present invention more economically, as compared with the above-mentioned case in which the compound represented by the formula [7] is used as the raw material.

Furthermore, the present inventors have found that the reaction of the first process proceeds with high selectivity under a particular reaction condition (i.e., at a relatively low temperature of 70° C. or lower).

It is generally known that aromatic compounds are brought into contact with hydrogen in the presence of a transition metal catalyst to generate a reaction in which the aromatic ring of the aromatic compound is reduced into a cyclohexyl ring. This reaction, however, often requires high temperature and high reaction pressure. For example, S. J. Lapporte, W. R. Schuett, Journal of Organic Chemistry, Vol. 28, pp. 1947-1948, 1963 discloses a reaction represented by the following formula.

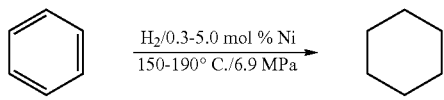

This reaction requires a temperature of 150-190° C. and a pressure of 6.9 MPa. Thus, it is necessary to use a special reactor that is resistant against such severe condition, and the operation becomes complicated for the synthesis in large amount. Furthermore, there is a fear of the decomposition of trifluoromethyl group in the case of the substrate of the present invention.

In contrast, it was found by the present invention that the reaction of the first process proceeds with sufficiently high reaction rate even at the above-mentioned relatively low temperature. Furthermore, it was found that the target compound can be obtained with particularly high selectivity at such temperature (see Example 1 of the specification). Therefore, it became significantly easy by the present invention to produce the target fluorine-containing diol represented by the formula [2] in large scale.

It is possible by a second process of the present invention to easily produce a fluorine-containing ester that has a bright prospect as a monomer raw material of the next generation resist materials and is represented by the formula [4],

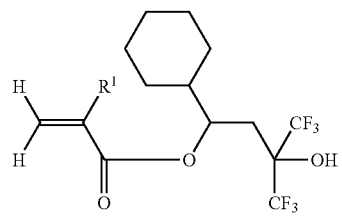

wherein $R^1$ represents H, $C_mH_{2m+1}$, or $C_nF_{2n+1}$ where each of m and n represents independently an integer of 1 to 4.

The second process comprises reacting the fluorine-containing diol represented by the formula [2], which is the product of the first process, with an acrylic acid derivative represented by the formula [3],

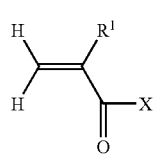

wherein $R^1$ is defined as in the formula [4], and X represents F, Cl, or a group represented by the formula [3a],

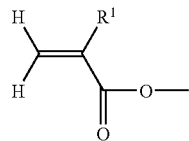

wherein $R^1$ is defined as in the formula [4].

It is possible to conduct each of the first and second processes by using a batch-wise reaction apparatus. The reaction conditions are exemplarily described in detail in the following. Certain modifications of the reaction conditions can be made by a person skilled in the art in respective reaction apparatuses.

The first process (the first step) is essential in the present invention, and according to need the second process (the second step) may be conducted, as shown in the following reaction scheme.

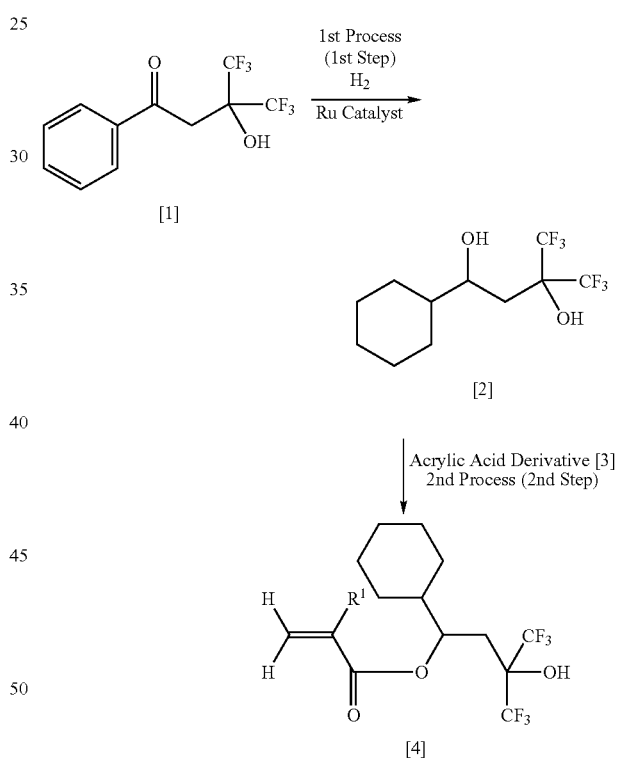

The first step for obtaining the fluorine-containing diol represented by the formula [2] is described in detail, as follows.

The starting material of the first step, the hydroxy ketone represented by the formula [1], can be synthesized by a known process disclosed in U.S. Pat. No. 3,662,071.

The reaction temperature for conducting the first step may be 0 to 150° C., preferably 10 to 120° C., more preferably 30 to 70° C. If it is lower than 0° C., the reaction rate may become too low to be of a practical process. If it is higher than 100° C. (e.g., at 110° C.), the production of a by-product represented by the formula [8],

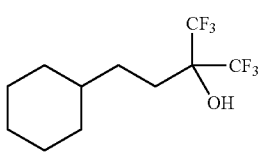

[8]

starts to increase, thereby decreasing selectivity of the target compound (see Example 2). In particular, selectivity of the target compound is further decreased by a reaction temperature exceeding 150° C. This reaction temperature may be economically not preferable from the viewpoint of energy efficiency, too.

By adjusting the reaction temperature to 30-70° C., particularly 40-60° C. (e.g., 50° C.), it is possible to obtain the target fluorine-containing diol represented by the formula [2] with a very high selectivity without producing the by-product represented by the formula [8]. Therefore, such reaction temperature is one of the most preferable reaction conditions of the first process (see Example 1).

The reaction pressure (hereinafter, referred to as hydrogen pressure) of the first step may be normally 0.1-6 MPa (in terms of absolute pressure, hereinafter the same), preferably 0.15-4.0 MPa, particularly preferably 0.2-4.0 MPa. The preferable reaction pressure depends on the reaction temperature. In other words, in case that the reaction is conducted at a relatively high temperature (80° C. or higher), the reaction proceeds with a sufficiently high reaction rate even if the reaction pressure is 1.0 MPa or lower. This reaction pressure is often preferable. In contrast, in case that the reaction is conducted at a low temperature (lower than 80° C.), it is often preferable to have a higher reaction pressure (e.g., 1.6 MPa or higher). For example, in case that the reaction is conducted at a temperature of 30-70° C., the reaction pressure is particularly preferably 1.6 to 4.0 MPa. It is preferable to optimize the reaction pressure depending on various conditions such as the reaction temperature, and the type and the amount of the after-mentioned catalyst.

The reaction proceeds even if the reaction pressure is lower than 0.1 MPa. In this case, it may be necessary to have a reaction temperature higher than 150° C. to have a sufficiently high reaction rate. This is not preferable since side reactions are accelerated. On the other hand, a reaction pressure exceeding 6 MPa requires having a reaction vessel that is resistant against such high pressure, and the operation becomes complicated. Therefore, such reaction pressure is not preferable.

The ruthenium catalyst used in the first step can be selected from (a) metallic ruthenium, (b) a solid-phase ruthenium catalyst in which ruthenium is carried on a carrier (e.g., activated carbon, alumina, silica, and clay), (c) a ruthenium salt (e.g., $RuCl_3$, $RuBr_3$, and $Ru(NO_3)_3$), (d) a ruthenium complex (e.g., $Ru(CO)_5$, $Ru(NO)_5$, $K_4[Ru(CN)_6]$, and $Ru(phen)_3Cl_3$ where phen represents a phenanthroline), and (e) ruthenium oxide.

The ruthenium catalyst used in the first step is preferably a solid phase catalyst in which ruthenium is carried on a carrier (e.g., activated carbon, alumina, and silica), from the viewpoints of availability and handling easiness. The solid phase catalyst can be prepared, for example, by impregnating a carrier with a ruthenium salt solution, followed by a reduction treatment with $H_2$ gas under heating. In particular, it is possible to easily obtain Ru/C (ruthenium-carbon catalyst in which ruthenium is carried on activated carbon), ruthenium-alumina catalyst, and ruthenium-silica catalyst as commercial products. These catalysts are preferable due to their high activities. These catalysts can particularly easily be handled, if they contain a certain amount of water (e.g., 50 wt % of water base on the total weight of the catalyst). Although the catalyst is not particularly limited with respect to the ruthenium content of the catalyst solid matter (i.e., the component other than water), that of about 2-10 wt % (e.g., 5 wt %) is preferable due to its easy availability, high stability and easy handling.

The reaction of the first step can be conducted in the presence of a plurality of ruthenium catalysts. However, such reaction does not have a particular merit.

The amount of the ruthenium catalyst used in the first step may be 0.0002 to 0.04 moles, preferably 0.0004 to 0.02 moles, more preferably 0.001 to 0.01 moles, in terms of mole number of Ru atoms, per mol of the hydroxy ketone represented by the formula [1]. If it is less than 0.0002 moles per that, the reaction rate may become too low. The use of greater than 0.04 moles per that is economically not preferable.

The above-explained ruthenium catalyst is highly stable and therefore can be used in the air. It is, however, particularly effective to conduct the reaction under a condition that the atmosphere of the reactor has been replaced with hydrogen gas to remove the air (oxygen) from the reactor. With this, it is possible to maintain the ruthenium catalyst activity to a higher level.

It is possible to use solvent for conducting the first step. The type of the solvent usable is not particularly limited. Its examples include ethers (e.g., diethyl ether, methyl-t-butyl ether, diisopropyl ether, and tetrahydrofuran), and alcohols (e.g., methanol, ethanol, propanol, 2-propanol, trifluoroethanol, and 1,1,1,3,3,3-hexafluoro-2-propanol). These solvents can be used singly or in combination. The solvent for the first step may be in an amount of 0.005 to 100 g, preferably 0.01 to 20 g, more preferably 0.1 to 10 g, per gram of the hydroxy ketone represented by the formula [1]. Exceeding 100 g may be economically not preferable from the viewpoint of productivity.

The reactor used in each of the first step, and the aftermentioned first and second cases of the second step may be made of a resin material (e.g., ethylene tetrafluoride resin, chlorotrifluoroethylene resin, vinylidene fluoride resin, and PFA resin). It may be one lined with glass or the like. Furthermore, it may be a glass or stainless steel vessel.

For example, the first step for producing the fluorine-containing diol represented by the formula [2] can be conducted, as follows. At first, a reactor proof against the reaction conditions of the first step is charged with the hydroxy ketone represented by the formula [1], solvent and the ruthenium catalyst. The reaction is conducted under heating from outside, while hydrogen gas is supplied into the reactor. The period of time required for the reaction depends on the reaction temperature, and the type and the amount of the catalyst. It is preferable to terminate the reaction at a time when the consumption of $H_2$ has been virtually finished, while observing the $H_2$ consumption condition at certain intervals based on the pressure of the reactor or the like. The consumption of the raw material is monitored by sampling or the like. Once the termination of the reaction has been found by monitoring the consumption of the raw material, the reaction liquid is cooled down. The resulting fluorine-containing diol represented by the formula [2] can be purified by a normal conventional method. For example, the catalyst is separated from the reaction liquid by filtration, and then the resulting filtrate is subjected to distillation or crystallization. With this, it is possible to easily obtain the target compound.

The second step for producing the fluorine-containing ester represented by the formula [4] is explained in detail, as follows.

The substituent $R^1$ of the acrylic acid derivative represented by the formula [3] is particularly preferably a hydrogen atom, methyl group or trifluoromethyl group, due to the usefulness of the target product represented by the formula [4] having such $R^1$.

The second step may be conducted by a normal esterification. Its particulars are described in detail, as follows. At first, there is described in detail a first case of the second step that the acrylic acid derivative represented by the formula [3] is an α-substituted acrylic halide (i.e., X=Cl or F in the formula [3]).

In the first case, it is preferable to conduct the second step in the presence of a base. This base is preferably at least one selected from trimethylamine, triethylamine, pyridine, 2,6-dimethylpyridine, dimethylaminopyridine, sodium carbonate, potassium carbonate, sodium hydroxide, and potassium hydroxide. Of these, pyridine and 2,6-dimethylpyridine are particularly preferable.

The above base to used in the second step may be in an amount of 0.2 to 2.0 moles, preferably 0.5 to 1.5 moles, more preferably 0.9 to 1.2 moles, per mol of the fluorine-containing diol represented by the formula [2]. If it is less than 0.2 moles per that, selectivity of the reaction and yield of the target product may become too low. If it exceeds 2.0 moles, the amount of the base that is not involved in the reaction may become too much. Thus, this may be economically not preferable.

The α-substituted acrylic halide to be used in the second step may be in an amount of 0.2 to 2.0 moles, preferably 0.5 to 1.5 moles, more preferably 0.9 to 1.2 moles, per mol of the fluorine-containing diol. If it is less than 0.2 moles per that, selectivity of the reaction and yield of the target product may become too low. If it exceeds 2.0 moles per that, the amount of the α-substituted acrylic halide that is not involved in the reaction may become too much. This increases a waste disposal load and thus may be economically not preferable.

In case that the acrylic acid derivative represented by the formula [3] is an α-substituted acrylic halide, a hydrofluoride or hydrochloride of the base precipitates as a by-product in the second step. In this case, it is necessary to use solvent to improve operability of the reaction. The type of this solvent is not particularly limited. Its examples include aromatic compounds (e.g., benzene, toluene, xylene, and mesitylene), ethers (e.g., diethyl ether, methyl-t-butyl ether, diisopropyl ether, and tetrahydrofuran), and halogen-containing compounds (e.g., methylene chloride, chloroform, and carbon tetrachloride). These solvents can be used singly or in combination.

The above-mentioned solvent may be in an amount of 0.5 to 100 g, preferably 1.0 to 20 g, more preferably 2.0 to 10 g, per gram of the fluorine-containing diol. If it is less than 0.5 g per that, the slurry concentration of the hydrofluoride or hydrochloride of the base may become too high, thereby lowering the operability. Exceeding 100 g per that may be economically not preferable from the viewpoint of the productivity.

In the first case of the second step, the reaction temperature may be −50 to 200° C., preferably −20 to 150° C., more preferably 0 to 120° C. If it is lower than −50° C., the reaction rate may become too low to be of a practical production process. If it is higher than 200° C., the raw material α-substituted acrylic halide or the target fluorine-containing ester represented by the formula [2] may polymerize. Thus, this may be not preferable.

In the first case of the second step, it is optional to conduct the reaction in the presence of a polymerization inhibitor for the purpose of suppressing polymerization of the α-substituted acrylic halide or the fluorine-containing ester. The polymerization inhibitor may be at least one compound selected from hydroquinone, p-methoxyphenol, 2,5-di-t-butylhydroquinone, 1,2,4-trihydroxybenzene, 2,5-bistetramethylbutylhydroquinone, leucoquinizarin, phenothiazine, 2-methoxyphenothiazine, tetraethylthiuram disulfide, 1,1-diphenyl-2-picrylhydrazyl, and 1,1-diphenyl-2-picrylhydrazine. Further examples of the polymerization inhibitor expressed in trade name, together with compound name in parenthesis, include NONFLEX F (N,N'-di-2-naphthyl-p-phenylenediamine), NONFLEX H (N,N'-diphenyl-p-phenylenediamine), NONFLEX DCD (4,4'-bis(α,α'-dimethyl benzyl)diphenylamine), NONFLEX MBP (2,2'-methylene-bis(4-methyl-6-tert-butylphenol), and OZONONE 35 (N-(1-methylheptyl)-N'-phenyl-p-phenylenediamine) of SEIKO CHEMICAL Co., Ltd located in Japan, and Q-1300 (N-nitrosophenylhydroxylamine ammonium salt) and Q-1301 (N-nitrosophenylhydroxylamine aluminum salt) of Wako Pure Chemical Industries, Ltd. located in Japan. All of the above examples of the polymerization inhibitor are easily available as commercial products.

In the first case of the second step, the polymerization inhibitor may be in an amount of 0 to 0.1 moles, preferably 0.00001 to 0.05 moles, more preferably 0.0001 to 0.01 moles, per mol of the fluorine-containing diol. Even if it exceeds 0.1 moles per that, the effect of suppressing the polymerization may not improve further. Thus, this may be economically not preferable.

In the following, there is described in detail a second case of the second step that the acrylic acid derivative represented by the formula [3] is an α-substituted acrylic acid anhydride (i.e., X of the formula [3] represents a group represented by the formula [3a]).

In the second case of the second step, the α-substituted acrylic acid anhydride may be in an amount of 0.5 to 5.0 moles, preferably 0.7 to 3.0 moles, more preferably 1.0 to 2.0 moles, per mol of the fluorine-containing diol. If it is less than 0.5 moles per that, conversion of the reaction and yield of the target product may become insufficient. If it is greater than 5.0 moles per that, the amount of the α-substituted acrylic acid anhydride that is not involved in the reaction may become too much. This may be economically not preferable due to the waste disposal load.

In the second case of the second step, it is possible to add an additive to accelerate the reaction. This additive is preferably at least one acid selected from organic sulfonic acids (e.g., methanesulfonic acid, ethanesulfonic acid, p-toluenesulfonic acid, benzenesulfonic acid, and trifluoromethanesulfonic acid) and Lewis acids. The additive may be in an amount of 0.01 to 2.0 moles, preferably 0.02 to 1.8 moles, more preferably 0.05 to 1.5 moles, per mol of the fluorine-containing diol. If it is less than 0.01 moles per that, conversion of the reaction and yield of the target product may become too low. If it is greater than 2.0 moles per that, the amount of the additive that is not involved in the reaction may become too much. This may be economically not preferable.

In the second case of the second step, if the additive is not added, the reaction temperature may be 80 to 200° C., preferably 100 to 180° C., more preferably 120 to 160° C.

If it is lower than 80° C., the reaction rate may become too low. If it is higher than 200° C., the α-substituted acrylic acid anhydride or the fluorine-containing ester may polymerize. In contrast, if the additive is added in the second case of the second step, it may be 0 to 80° C., preferably 10 to 70° C., more preferably 20 to 60° C. If it is lower than 0° C., the reaction rate may become too low to be of a practical production process. If it is higher than 80° C., side reactions tend to occur, thereby lowering selectivity of the target fluorine-containing ester. Thus, it is preferable to add the additive in the second case of the second step, since it is possible to obtain a sufficient reactivity and an improved selectivity with a relatively low temperature. For example, it is a particularly preferable embodiment in the second case of the second step that the reaction is conducted at a temperature of 20 to 60° C. in the presence of an additive that is at least one acids selected from methanesulfonic acid, ethanesulfonic acid, p-toluenesulfonic acid, benzensulfonic acid, and trifluoromethanesulfonic acid.

In the second case of the second step, the reaction can proceed without solvent. It is, however, preferable to use solvent in order to obtain homogeneity of the reaction and to improve operability after the reaction. The type of the solvent is not particularly limited. Its examples may be the same as those used in the first case of the second step. Such solvents may be used singly or in combination.

The solvent to be used in the second case of the second step may be 0.1 to 100 g, preferably 0.5 to 50 g, more preferably 1.0 to 20 g, per gram of the fluorine-containing diol. If it is less than 0.1 g per that, the merit of using the solvent may be insufficient. Exceeding 100 g per that may be economically not preferable from the viewpoint of productivity.

In the second case of the second step, it is optional to conduct the reaction in the presence of a polymerization inhibitor for the purpose of suppressing polymerization of the α-substituted acrylic acid anhydride or the fluorine-containing ester. The polymerization inhibitor may be at least one compound selected from hydroquinone, p-methoxyphenol, 2,5-di-t-butylhydroquinone, 1,2,4-trihydroxybenzene, 2,5-bistetramethylbutylhydroquinone, leucoquinizarin, phenothiazine, 2-methoxyphenothiazine, tetraethylthiuram disulfide, 1,1-diphenyl-2-picrylhydrazyl, and 1,1-diphenyl-2-picrylhydrazine. Further examples of the polymerization inhibitor expressed in trade name include NONFLEX F, NONFLEX H, NONFLEX DCD, NONFLEX MBP, and OZONONE 35 of SEIKO CHEMICAL Co., Ltd located in Japan, and Q-1300 and Q-1301 of Wako Pure Chemical Industries, Ltd. located in Japan.

In the second case of the second step, the polymerization inhibitor may be in an amount of 0.00001 to 0.1 moles, preferably 0.0001 to 0.05 moles, more preferably 0.001 to 0.01 moles, per mol of the fluorine-containing diol. Even if it exceeds 0.1 moles per mol of that, the effect of suppressing the polymerization may not improve further. Thus, this may be economically not preferable.

For example, it is possible to conduct the first case of the second step that the acrylic acid derivative represented by the formula [3] is an α-substituted acrylic halide (i.e., X=Cl or F in the formula [3]), for producing the fluorine-containing ester represented by the formula [2], as follows. At first, a reactor proof against the reaction conditions is charged with base, solvent, the fluorine-containing diol represented by the formula [2], the α-substituted acrylic halide and polymerization inhibitor. Then, the reaction is conducted with stirring under heating from outside. The consumption of the raw material is monitored by sampling or the like. Once the termination of the reaction has been found by monitoring the consumption of the raw material, the reaction liquid is cooled down.

The fluorine-containing ester obtained in the first case of the second step can be purified by a normal conventional method. For example, a hydrochloride of the base, contained in the reaction liquid, is removed by filtration. The resulting filtrate is sequentially treated with a hydrochloric acid aqueous solution, a sodium carbonate aqueous solution, and a sodium chloride aqueous solution in this order, followed by distilling the solvent out, thereby obtaining a crude organic matter. This crude organic matter can be purified, for example, by column chromatography or distillation, thereby obtaining the target product of high purity.

For example, it is possible to conduct the second case of the second step that the acrylic acid derivative represented by the formula [3] is an α-substituted acrylic acid anhydride (i.e., X of the formula [3] represents a group represented by the formula [3a]), for producing the fluorine-containing ester represented by the formula [4], as follows. At first, a reactor proof against the reaction conditions is charged with solvent, the fluorine-containing diol represented by the formula [2], the α-substituted acrylic acid anhydride, polymerization inhibitor and additive. Then, the reaction is conducted with stirring under heating from outside. The consumption of the raw material is monitored by sampling or the like. Once the termination of the reaction has been found by monitoring the consumption of the raw material, the reaction liquid is cooled down.

The fluorine-containing ester obtained in the second case of the second step can be purified by a normal conventional method. For example, the reaction liquid is sequentially treated with water, a sodium hydrogen carbonate aqueous solution, and brine in this order, followed by distilling the solvent out, thereby obtaining a crude organic matter. This crude organic matter can be purified, for example, by column chromatography or distillation, thereby obtaining the target product of high purity.

The following nonlimiting examples are illustrative of the present invention. Herein, the percent (%) of the compositional analysis value refers to areal % of an organic component obtained by gas chromatography of a sampled reaction mixture.

EXAMPLE 1 (1st Step)

Production of 1-cyclohexyl-4,4,4-trifluoro-3-(trifluoromethyl)butane-1,3-diol

A 1L pressure-proof stainless steel reactor equipped with a pressure gauge, a thermometer and a stirrer was charged with 355 g of diisopropyl ether, 350 g (1.22 moles) of 4,4,4-trifluoro-3-hydroxy-1-phenyl-3-(trifluoromethyl)butan-1-one and 35.0 g of 5% Ru/C (i.e., a ruthenium catalyst wherein Ru is carried on activated carbon; water content: 50%; made by N.E. CHEMCAT CORPORATION located in Tokyo, Japan). The atmosphere of the reactor was replaced with hydrogen. Then, the reaction was conducted at an internal temperature of 50° C. and under a reaction pressure (absolute pressure) of 2.6 MPa by heating the reactor in an oil bath. 16 hr later the temperature was lowered to room temperature, thereby terminating the reaction. The sampled reaction liquid, except diisopropyl ether used as a solvent, was found by gas chromatography to contain 96.0% of 1-cyclohexyl-4,4,4-trifluoro-3-(trifluoromethyl)butane-1,3-diol and 4.0% of others. The ruthenium catalyst was separated from the reaction liquid by filtration. Then, the solvent was distilled out of the filtrate, followed by recrystallization from hexane, thereby obtaining 318.2 g of the target 1-cyclohexyl-4,4,4-trifluoro-3-(trifluoromethyl)butane-1,3-diol (purity: 97.5%). The yield was 91%.

Identification data of the target product are as follows.

$^1$H NMR (solvent: CDCl$_3$; standard substance: TMS); δ 4.01 (s, 1H), 6.31 (s, 1H), 2.2 (m, 2H), 2.06 (m, 3H), 1.60 (m, 6H), 1.21 (m, 3H). $^{19}$F NMR (solvent: CDCl$_3$; standard substance: CCl$_3$F); δ−75.9 (d, J=10.7 Hz, 3F), −72.9 (d, J=9.16 Hz, 3F). CI MS m/z (relative intensity): 277(100.0), 211 (26.3), 83 (55.8).

EXAMPLE 2 (1st Step)

Production of 1-cyclohexyl-4,4,4-trifluoro-3-(trifluoromethyl)butane-1,3-diol

A 100 ml pressure (10 MPa) proof stainless steel reactor equipped with a thermometer and a pressure gauge was charged with a stirring magnet coated with tetrafluoroethylene resin, 3.0 g (0.010 moles) of 4,4,4-trifluoro-3-hydroxy-1-phenyl-3-(trifluoromethyl)butan-1-one, 0.3 g (10 wt %) of 5% Ru/C, and 10 mL of diisopropyl ether. The atmosphere of the reactor was replaced with hydrogen. Then, hydrogen was continuously introduced into the reactor in a manner to have a hydrogen pressure of 0.6 MPa (in terms of absolute pressure) with stirring using a stirrer, while the reactor was heated in an oil bath at 110° C. 4 hr later the termination of the decrease of the internal pressure was confirmed, followed by cooling to room temperature. The reaction liquid, except diisopropyl ether used as a solvent, was found by gas chromatography to contain 69.0% of 1-cyclohexyl-4,4,4-trifluoro-3-(trifluoromethyl)butane-1,3-diol, 29.9% of 4-cyclohexyl-1,1,1-trifluoro-2-(trifluoromethyl)butan-2-ol, and 1.1% of others.

EXAMPLE 3 (2nd Step)

Production of 1-cyclohexyl-4,4,4-trifluoro-3-hydroxy-3-(trifluoromethyl)butyl 2-methylacrylate A 1-liter, three-necked, glass flask equipped with a stirrer, a thermometer and a reflux condenser was charged with 296.5 g (1 mol) of 1-cyclohexyl-4,4,4-trifluoro-3-(trifluoromethyl)butane-1,3-diol, 170.8 g (1.1 moles) of methacrylic anhydride, 1.0 g of trifluoromethanesulfonic acid, and 0.1 g of 2-methoxyphenothiazine as a polymerization inhibitor, followed by heating at 130° C. with stirring. 3 hr later, when conversion of the raw material 1-cyclohexyl-4,4,4-trifluoro-3-(trifluoromethyl)butane-1,3-diol became 99% or higher, the reaction was terminated. The reaction mixture was cooled down to room temperature, followed by distillation under reduced pressure to collect a distillate having a boiling point range of 112-115° C./0.09 kPa. With this, there were obtained 312.8 g of the target 1-cyclohexyl-4,4,4-trifluoro-3-hydroxy-3-(trifluoromethyl)butyl 2-methylacrylate (purity: 96%). The yield was 90%.

Identification data of the target product are as follows.

$^1$H NMR (solvent: CDCl$_3$; standard substance: TMS); δ 6.19 (d, J=1.2, 1H), 5.68 (d, J=1.2, 1H), 4.89 (dt, J=3.9, 4.1, 1H), 2.41 (dd, J=3.4, 3.7, 1H), 2.11 (dd, 1.2, 2.2, 1H), 1.96 (s, 3H), 1.76 (m, 6H), 1.20 (m, 6H). $^{19}$F NMR (solvent: CDCl$_3$; standard substance: CCl$_3$F); δ−77.07 (q, J=9.1 Hz, 3F), −79.39 (q, J=9.1 Hz, 3F). CI MS m/z (relative intensity): 69 (100), 276 (24), 362 (M$^+$, 0.6).

COMPARATIVE EXAMPLE

A 100 mL pressure-proof glass reactor equipped with a pressure gauge, a thermometer and a stirrer was charged with 10.4 g (0.04 moles) of 4,4,4-trifluoro-3-hydroxy-1-phenyl-3-(trifluoromethyl)butan-1-one, 1.0 g of 10% Pd/C (i.e., a palladium catalyst wherein Pd is carried on activated carbon; water content: 50%; made by N.E. CHEMCAT CORPORATION located in Tokyo, Japan), and 20 mL of diisopropyl ether. The atmosphere of the reactor was replaced with hydrogen. Then, hydrogen was continuously introduced into the reactor at 1.0 MPa (absolute pressure) with heating at 40° C. 12 hr later the temperature was lowered to room temperature, thereby obtaining 24.5 g of a reaction mixture. The sampled reaction liquid, except diisopropyl ether used as a solvent, was found by gas chromatography to contain 97.1% of 4,4,4-trifluoro-1-phenyl-3-(trifluoromethyl)butane-1,3-diol and 2.9% of others. The palladium catalyst was separated from this reaction mixture by filtration. Then, the solvent was distilled out of the filtrate, followed by distillation under reduced pressure to collect a distillate having a boiling point range of 140-143° C./2.0 kPa. With this, there were obtained 7.97 g of 4,4,4-trifluoro-1-phenyl-3-(trifluoromethyl)butane-1,3-diol (purity: 98.6%). The yield was 76.1%.

Identification data of the product are as follows.

$^1$H NMR (solvent: CDCl$_3$; standard substance: TMS); δ7.24-7.34 (m, 5H), 6.41 (s, 1H), 5.24 (d, J=11.7 Hz, 1H), 2.91 (s, 1H), 2.18-2.40 (m, 2H). $^{19}$F NMR (solvent: CDCl$_3$; standard substance: CCl$_3$F); δ −75.8 (q, J=9.92 Hz, 3F), −79.7 (q, J=9.92 Hz, 3F). EI-MS m/z (relative intensity): 288 (M$^+$, 0.8), 201 (3.5), 109 (3.4), 107 (100), 79 (63), 77 (35), 69 (8.8), 51 (12).

As above, it was not possible by Comparative Example to obtain 1-cyclohexyl-4,4,4-trifluoro-3-(trifluoromethyl)butane-1,3-diol, which is the target compound of the first step of the present invention.

What is claimed is:

1. A process for producing a fluorine-containing diol represented by the formula [2],

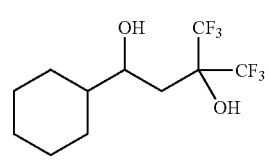

[2]

the process comprising reducing a hydroxy ketone represented by the formula [1],

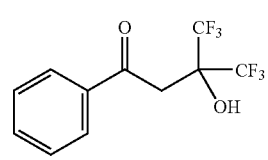

[1]

by hydrogen in the presence of a ruthenium catalyst.

2. A process according to claim 1, wherein the reducing is conducted at a reaction temperature of 10 to 120° C.

3. A process according to claim 1, wherein the reducing is conducted at a reaction temperature of 30 to 70° C.

4. A process according to claim 1, wherein the ruthenium catalyst is one selected from the group consisting of metallic ruthenium, ruthenium carried on a carrier, a ruthenium salt, a ruthenium complex, and ruthenium oxide.

5. A process according to claim 4, wherein the ruthenium salt is selected from the group consisting of $RuCl_3$, $RuBr_3$, and $Ru(NO_3)_3$, and the ruthenium complex is selected from the group consisting of $Ru(CO)_5$, $Ru(NO)_5$, $K_4[Ru(CN)_6]$, and $Ru(phen)_3Cl_3$ where phen represents a phenanthroline.

6. A process according to claim 4, wherein the ruthenium catalyst is a solid-phase catalyst in which ruthenium is carried on an activated carbon, alumina, or silica.

7. A process according to claim 1, wherein, prior to the reducing, atmosphere of a reactor for conducting the reducing is replaced with hydrogen gas.

8. A process according to claim 1, wherein the reducing is conducted in a solvent that is at least one selected from the group consisting of ethers and alcohols.

9. A process according to claim 8, wherein the ethers are diethyl ether, methyl-tert-butyl ether, diisopropyl ether and tetrahydrofuran, and the alcohols are methanol, ethanol, propanol, 2-propanol, trifluoroethanol and 1,1,1,3,3,3-hexafluoro-2-propanol.

10. A process according to claim 1, wherein the reducing is conducted at a temperature of 30 to 70° C. under a hydrogen pressure of 1.6 to 4.0 MPa.

11. A process according to claim 1, wherein the ruthenium catalyst is in an amount of 0.0002 to 0.04 moles, in terms of Ru atoms of the ruthenium catalyst, per mol of the hydroxy ketone.

12. A process for producing a fluorine-containing ester represented by the formula [4],

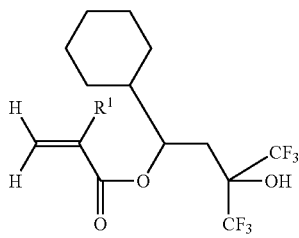

[4]

wherein $R^1$ represents H, $C_mH_{2m+1}$, or $C_nF_{2n+1}$ where each of m and n represents independently an integer of 1 to 4, the process comprising the steps of:

(a) reducing a hydroxy ketone represented by the formula [1],

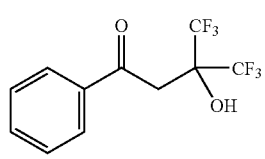

[1]

by hydrogen in the presence of a ruthenium catalyst, thereby producing a fluorine-containing diol represented by the formula [2],

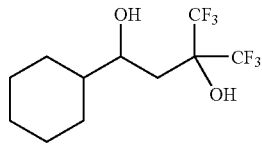

[2]

and (b) reacting the fluorine-containing diol with an acrylic acid derivative represented by the formula [3],

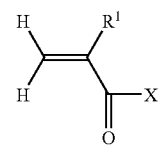

[3]

wherein $R^1$ is defined as in the formula [4], and X represents F, Cl, or a group represented by the formula [3a],

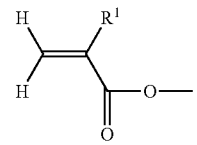

[3a]

wherein $R^1$ is defined as in the formula [4].

13. A process according to claim 12, wherein $R^1$ of the formula [4] represents H, methyl group or trifluoromethyl group.

14. A process according to claim 12, wherein, when X of the formula [3] represents F or Cl, the step (b) is conducted in the presence of a base.

15. A process according to claim 14, wherein the base is pyridine or 2,6-dimethylpyridine.

16. A process according to claim 14, wherein the base is in an amount of 0.2 to 2 moles per mol of the fluorine-containing diol.

17. A process according to claim 12, wherein X of the formula [3] represents the group, represented by the formula [3a], the step (b) is conducted at a temperature of 20-60° C. in the presence of an additive that is at least one selected from the group consisting of methanesulfonic acid, ethanesulfonic acid, p-toluenesulfonic acid, benzensulfonic acid, and trifluoromethanesulfonic acid.

18. A process according to claim 12, wherein the step (b) is conducted in a solvent that is at least one selected from the group consisting of aromatic compounds, ethers, and halogen-containing compounds.

19. A process according to claim 18, wherein the aromatic compounds are benzene, toluene, xylene, and mesitylene; the ethers are diethyl ether, methyl-t-butyl ether, diisopropyl ether, and tetrahydrofuran; and the halogen-containing compounds are methylene chloride, chloroform, and carbon tetrachloride.

20. A process according to claim 12, wherein the step (b) is conducted in the presence of a polymerization inhibitor.

* * * * *